(12) United States Patent
James et al.

(10) Patent No.: US 6,520,993 B2
(45) Date of Patent: Feb. 18, 2003

(54) SPINAL IMPLANT

(75) Inventors: Stephen B. James, Rochester, NY (US); Billy G. Anderson, Virginia Beach, VA (US); John D. Malone, Cumberland, RI (US); Bradley T. Moore, Barrington, RI (US); Ronald J. Naughton, South Dartmouth, MA (US)

(73) Assignees: DePuy Acromed, Inc., Raynham, MA (US); Lifenet, Virginia Beach, VA (US)

( * ) Notice: Subject to any disclaimer, the term of this patent is extended or adjusted under 35 U.S.C. 154(b) by 131 days.

(21) Appl. No.: 09/753,233

(22) Filed: Dec. 29, 2000

(65) Prior Publication Data

US 2002/0087212 A1 Jul. 4, 2002

(51) Int. Cl.[7] .................................................. A61F 2/44
(52) U.S. Cl. .................................................. 623/17.16
(58) Field of Search .......................... 623/17.11, 17.16, 623/17.13, 17.15; 606/61; D24/155

(56) References Cited

U.S. PATENT DOCUMENTS

| | | |
|---|---|---|
| 4,272,855 A | 6/1981 | Frey |
| 4,349,921 A | 9/1982 | Kuntz |
| 4,627,853 A | 12/1986 | Campbell et al. |
| 4,678,470 A | 7/1987 | Nashef et al. |
| 4,685,919 A | 8/1987 | Niwa et al. |
| 4,759,769 A | 7/1988 | Hedman et al. |
| 4,834,757 A | 5/1989 | Brantigan |
| 4,950,296 A | 8/1990 | McIntyre |
| 5,053,049 A | 10/1991 | Campbell |
| 5,071,437 A | 12/1991 | Steffee |
| 5,092,893 A | 3/1992 | Smith |
| 5,192,327 A | 3/1993 | Brantigan |
| 5,245,098 A | 9/1993 | Summers et al. |
| 5,246,458 A | 9/1993 | Graham |
| 5,275,954 A | 1/1994 | Wolfinbarger et al. |
| 5,306,303 A | 4/1994 | Lynch |
| 5,306,307 A | 4/1994 | Senter et al. |

(List continued on next page.)

FOREIGN PATENT DOCUMENTS

| | | |
|---|---|---|
| EP | 0538183 | 4/1993 |
| FR | 2703580 | 10/1994 |
| WO | 9426213 | 11/1994 |
| WO | 9508306 | 3/1995 |
| WO | 9817209 | 4/1998 |
| WO | 9855052 | 12/1998 |
| WO | 9856319 | 12/1998 |
| WO | 9856433 | 12/1998 |
| WO | WO 01/49220 | 7/2001 |
| WO | WO 01/62191 | 8/2001 |
| WO | WO 01/66048 | 9/2001 |
| WO | WO 01/70137 | 9/2001 |
| WO | WO 01/78798 | 10/2001 |

OTHER PUBLICATIONS

*Surgical Technique Using FRA Spacer Instruments: Technique Guide*, Synthes Spine, pp. 1–16(1998).
*Keystone Graft Instruments*, Pamphlet by DePuy Motech, Inc., 6 pages (1998).

Primary Examiner—Eduardo C. Robert
(74) Attorney, Agent, or Firm—Nutter, McClennen & Fish LLP (57) ABSTRACT

An implantable spinal graft includes a substantially annular body with opposed superior and inferior surfaces. At least a portion of the superior and inferior surfaces includes a plurality of bone-engaging protrusions. Both of the superior and inferior surfaces also include at least one region that is free of protrusions. Preferably, the protrusion-free regions are centrally disposed and are oriented so as to be parallel to or angled with respect to an anterior-posterior axis of the implant. The implant further includes a tip on the posterior that is formed by converging portion of the superior and inferior surfaces.

29 Claims, 5 Drawing Sheets

U.S. PATENT DOCUMENTS

| | | |
|---|---|---|
| 5,306,308 A | 4/1994 | Gross et al. |
| 5,306,309 A | 4/1994 | Wagner et al. |
| 5,429,863 A | 7/1995 | McMillin |
| 5,443,514 A | 8/1995 | Steffee |
| 5,458,643 A | 10/1995 | Oka et al. |
| 5,514,180 A | 5/1996 | Heggeness et al. |
| 5,534,030 A | 7/1996 | Navarro et al. |
| 5,556,379 A | 9/1996 | Wolfinbarger |
| 5,571,109 A | 11/1996 | Bertagnoli |
| 5,609,635 A | 3/1997 | Michelson |
| 5,609,637 A | 3/1997 | Biedermann et al. |
| 5,658,337 A | 8/1997 | Kohrs et al. |
| 5,674,294 A | 10/1997 | Bainville et al. |
| 5,683,465 A | 11/1997 | Shinn et al. |
| 5,702,449 A | 12/1997 | McKay |
| 5,702,455 A | 12/1997 | Saggar |
| 5,722,977 A | 3/1998 | Wilhelmy |
| 5,725,579 A | 3/1998 | Fages et al. |
| 5,728,159 A | 3/1998 | Stroever et al. |
| 5,741,253 A | 4/1998 | Michelson |
| 5,766,251 A * | 6/1998 | Koshino ...................... 623/16 |
| 5,766,253 A | 6/1998 | Brosnahan, III |
| 5,776,196 A | 7/1998 | Matsuzaki et al. |
| 5,776,199 A | 7/1998 | Michelson |
| 5,785,710 A | 7/1998 | Michelson |
| 5,797,871 A | 8/1998 | Wolfinbarger, Jr. |
| 5,814,084 A | 9/1998 | Grivas et al. |
| 5,820,581 A | 10/1998 | Wolfinbarger, Jr. |
| 5,824,094 A | 10/1998 | Serhan et al. |
| 5,865,845 A | 2/1999 | Thalgott |
| 5,865,846 A | 2/1999 | Bryan et al. |
| 5,888,222 A | 3/1999 | Coates et al. |
| 5,888,227 A | 3/1999 | Cottle |
| 5,893,889 A | 4/1999 | Harrington |
| 5,897,593 A | 4/1999 | Kohrs et al. |
| 5,972,368 A | 10/1999 | McKay |
| 5,989,289 A | 11/1999 | Coates et al. |
| 6,143,033 A | 11/2000 | Paul et al. |
| 6,258,125 B1 | 7/2001 | Paul et al. |
| 6,261,586 B1 | 7/2001 | McKay |
| 6,270,528 B1 | 8/2001 | McKay |
| 6,277,149 B1 * | 8/2001 | Boyle et al. .............. 623/17.16 |
| D450,121 S * | 11/2001 | Anderson .................. D24/155 |
| 6,325,827 B1 * | 12/2001 | Lin .......................... 623/17.16 |
| 2001/0039456 A1 | 11/2001 | Boyer, II et al. |
| 2001/0039457 A1 | 11/2001 | Boyer, II et al. |
| 2001/0039458 A1 | 11/2001 | Boyer, II et al. |
| 2001/0041941 A1 | 11/2001 | Boyer, II et al. |
| 2001/0047208 A1 | 11/2001 | Michelson |
| 2001/0049560 A1 | 12/2001 | Paul et al. |
| 2001/0056302 A1 | 12/2001 | Boyer, II et al. |
| 2002/0026243 A1 * | 2/2002 | Lin .......................... 623/17.11 |
| 2002/0029084 A1 | 3/2002 | Paul et al. |
| 2002/0068977 A1 * | 6/2002 | Jackson .................. 623/17.15 |

\* cited by examiner

SPINAL IMPLANT

FIELD OF THE INVENTION

The invention relates to vertebral implants, and more particularly, to implants made from allograft bone, or other suitable materials, with dimensions and geometries suitable for placement between adjacent vertebral bodies.

BACKGROUND OF THE INVENTION

Disease, advancing age, and trauma can lead to changes in various bones, discs, joints, and ligaments of the body. Some changes and trauma often manifest themselves in the form of damage or degeneration to a spinal disc. This condition often results in chronic back pain, which can be anywhere from mild to severe. This pain can sometimes be eliminated by spinal fusion in which two adjacent vertebral bodies are joined together after removing the intervening intervertebral disc. A prosthetic device is usually placed between the two adjacent vertebral bodies, in place of the removed disc, to fill the space left by the removed disc and to allow bone to grow between the two vertebral bodies.

The success or failure of the fusion can often depend upon the type and properties of the prosthesis that is placed between the adjacent vertebral bodies. Obviously, the prosthesis must be sufficiently strong to withstand the loads encountered in the spine, it must be biocompatible, and it should permit the ingrowth of bone to complete the fusion. Perhaps more importantly, the prosthesis must have properties and geometries that permit the prosthesis to remain fixed in the desired position, without movement due to shifting, rotation, or slippage of the prosthesis.

A variety of prosthetic implants are known to exist. For example, a variety of artificial intervertebral discs are disclosed in U.S. Pat. Nos. 5,893,889; 5,683,465; 5,674,294; 5,458,643; 5,306,309; 5,246,458; and 4,759,769. Other known implantable prostheses for such applications include fusion cages made from metals and/or synthetic materials.

Many prostheses can also be fashioned from allograft bone that is harvested from portions of long bone including the femur, humerus, tibia, fibula, ulna and radius. An example of an allogenic intervertebral implant is disclosed in U.S. Pat. No. 6,143,033.

Despite known prostheses for the fusion of adjacent vertebral bodies, there remains a need for additional prostheses that have properties and geometries suitable for secure and effective implantation within a patient's spine.

SUMMARY OF THE INVENTION

An implantable bone graft is in the form of a solid annular body having opposed superior and inferior surfaces, and opposite anterior and posterior ends. The substantially central opening defined by the annular body extends between the superior and inferior surfaces and, during surgical implantation, the opening can be filled with a bone growth-promoting material. At least a portion of both the superior and inferior surfaces include a plurality of discrete protrusions or teeth. Each protrusion preferably has a base that is integral with one of the superior and inferior surfaces. Both the superior and inferior surfaces further include at least one region or band that is free of any protrusions. The protrusion-free band is preferably in a predetermined shape, such as rectangular, and is oriented in a desired direction. These bands preferably are centrally disposed on the superior and inferior surfaces and can be aligned so as to be parallel to an anterior-posterior axis of the body or angled with respect to the anterior-posterior axis of the body.

The body also includes a tip that is formed at the posterior end thereof. The tip is preferably formed by converging portions of superior and inferior surfaces. The tip may extend over a distance that represents ten to fifty percent of the anteriorposterior depth of the body.

In one embodiment, both the superior and inferior surfaces are canted such that the thickness dimension of the graft is greater at the anterior end than at the posterior end. Alternatively, both the superior and inferior surfaces can be oriented parallel to the anterior-posterior axis of the body. In yet another embodiment, the superior surface is oriented parallel to the anterior-posterior axis, but the inferior surface is angled such that the thickness of the graft is greater at the anterior end than at the posterior end. Both the superior and inferior surfaces can be substantially linear or, alternatively, they can have a dome-like profile, while still maintaining any inclination of the surface from the anterior to the posterior end.

BRIEF DESCRIPTION OF THE DRAWINGS

The invention will be more fully understood by reference to the following detailed description when considered in conjunction with the accompanying drawings, in which.

DETAILED DESCRIPTION OF THE INVENTION

The present invention provides an implantable spinal graft that can be used to fuse together adjacent vertebral bodies while maintaining the natural curve of the spine and the proper spacing between the adjacent vertebral bodies. The graft has a size and a geometry that enables it to be efficiently installed and to remain securely placed between adjacent vertebral bodies until healing and fusion take place.

Referring to FIGS. 1 through 5, the implant 10 is a solid annular body having a substantially central opening 12, surrounded by the ring-like body 14. The body 14 has opposed superior and inferior surfaces 16, 18 and anterior and posterior ends 20, 22. At least a portion of the superior and inferior surfaces, 16, 18, includes a plurality of bone-engaging protrusions 24. Preferably, these protrusions 24 are discrete. The superior and inferior surfaces, 16, 18 each include one or more zones or regions 26 that are free of any bone-engaging protrusions. The posterior end 22 of the implant includes a tip 28 that is formed of converging portions of the superior and inferior surfaces 16, 18.

Figure 1:
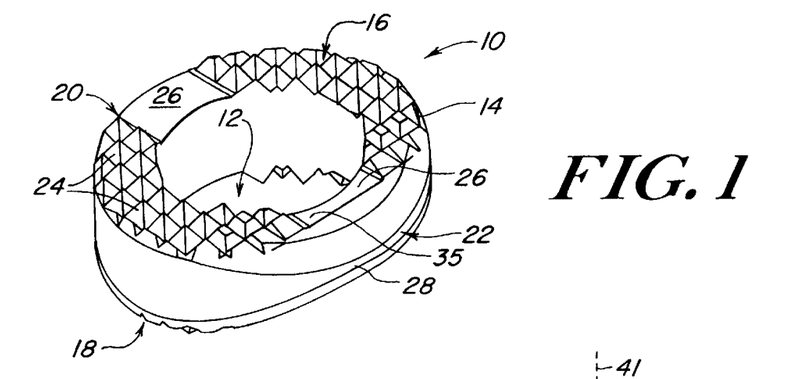
FIG. 1 is a perspective view of an intervertebral implant constructed according to the present invention.
Figure 2:
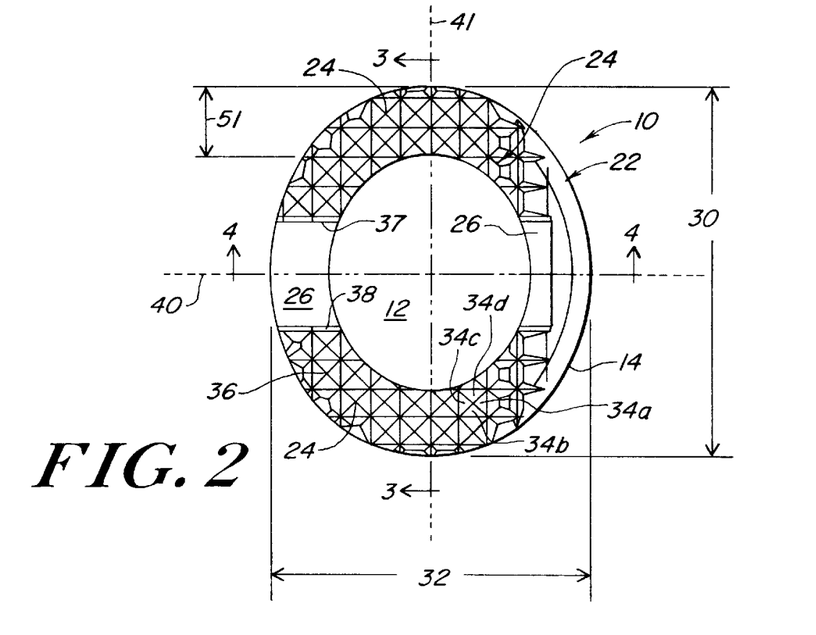
FIG. 2 is a top, plan view of the implant of FIG. 1.

As shown in FIGS. 1 and 2, the implant is of a size and shape that will enable it to fit within the intervertebral space, abutting the end plates of adjacent vertebral bodies. In one embodiment, the implant is shown as being substantially ovoid in shape, when viewed from the top, with the medial width 30 being greater than the anterior-posterior depth 32. One of ordinary skill in the art will appreciate that the implant may also take the form of an oval in which the anterior-posterior depth 32 is greater than the medial width 30. Moreover, the implant may also take the form of other shapes, including a circle, a square, and a rectangle.

For reference purposes, the implant 10 has an anterior-posterior axis 40 and a transverse axis 41.

The opening 12 is substantially centrally formed in the implant 10 and it extends through the superior 16 to the inferior surface 18 of the body 14. The opening 12 may have a regular or irregular shape. Preferably, however, the opening 12 has a regular shape, substantially in the form of a circle or oval.

The size of the opening can vary depending upon a variety of factors, including the size of the implant and the objectives relating to its use. Generally, the opening has an area that represents approximately 25% to 75% of the overall area (or "footprint") defined by the superior or inferior surfaces of the implant.

One of ordinary skill in the art will readily appreciate that the superior and inferior surfaces 16, 18 each include a variety of features. Each of the superior and inferior surfaces is preferably a mirror image of the other.

The superior and inferior surfaces, as noted above, each include a number of bone-engaging protrusions 24. Preferably, these protrusions extend from and are integral with one of the superior and inferior surfaces 16, 18 of the body. Although the protrusions 24 may take on a variety of shapes, they are preferably in the form of discrete, pyramid-shaped teeth. As shown in FIGS. 1 through 5, each protrusion 24 has four triangular-shaped sides 34a–d that meet at a point at the peak 36 of the pyramid. Preferably each side 34a–d is oriented at an angle ($\alpha_i$) that is in range of about 50 to 70 degrees, and most preferably about 60 degrees.

Each protrusion 24 should have a size sufficient to enable it to engage and penetrate any bone adjacent to which it is positioned. This bone-engaging feature facilitates the secure mounting of the implant within bone. In an exemplary embodiment each protrusion 24 preferably has a base with dimensions in the range of about 1 to 6 mm$^2$ and a height ($h_t$) in the range of about 0.5 to 7 mm.

As illustrated, the protrusions 24 are present on a majority of the surface area of the superior and inferior surfaces 16, 18. However, as described below, one or more regions are present on both the superior and inferior surfaces, in a defined pattern, in which no teeth are present. In addition, teeth are generally absent from the tip 28.

The protrusion-free zones 26 are present on each of the superior and inferior surfaces 16, 18. Preferably, each protrusion-free zone 26 is substantially centrally disposed on the superior and inferior surfaces 16, 18, and the protrusion-free zone 26 present on one surface is aligned with the complementary protrusion-free zone on the other surface.

The protrusion-free zones 26 provide a band or region within which no protrusions or teeth are present so as to enable the implant 10 to be grasped and manipulated by tools that will be used to implant this device. Generally, zones 26 are of a size and a shape that enable an insertion tool (not shown) with substantially elongate, rectangular grasping blades (not shown) to engage the implant while the blades remain recessed with respect to the peak 36 of protrusions 24. One important feature of the protrusion-free zones of the present invention is that these zones are not formed as channels that are cut into the superior and/or inferior surfaces 16, 18 of the body 10. Rather, they are relief zones that are formed by the selective removal of protrusions from an applicable region. In this way, the strength and integrity of the implant is maintained and it is believed to be less prone to failure, which could otherwise result if channels were created within the body.

The protrusion-free zones 26 serve to allow the implant to be handled and manipulated by an insertion tool. Thus, the zones 26 should be oriented in a manner that is convenient for the surgical approach that will be used to install the implant and which will allow for easy subsequent removal of the inserter tool once the implant 10 is surgically placed. For example, the protrusion-free zones 26 will extend substantially parallel to the anterior-posterior axis 40 of the implant 10 when an anterior surgical approach will be used to implant the device 10. If a lateral approach is to be used, the zone 26 generally extends orthogonally to the anterior-posterior axis of the implant, along transverse axis 41. Antero-lateral approaches can be accommodated by forming zones 26 that extend at an angle in the range of about 10 to 50 degrees with respect to the anterior-posterior axis 40. One of ordinary skill in the art will appreciate that more than one protrusion-free zone 26 may be formed on each of surfaces 16, 18.

FIGS. 1 through 5 illustrate an implant in which the protrusion-free zones 26 are oriented in a direction that is parallel to the anterior-posterior axis 40. Preferably, the zones 26 extend across an entire dimension of the implant 10, interrupted by opening 12. As shown in FIGS. 1, 2, 4, 6, and 10, zones 26 have a substantially U-shaped profile with a first (top or bottom) surface 35 that is defined by either the superior or inferior surfaces 16, 18. Second and third sides 37, 38 of zones 26 are defined laterally and medially by first and second rows 39, 43 of medial protrusions on both the superior and inferior surfaces 16, 18.

Figure 4:
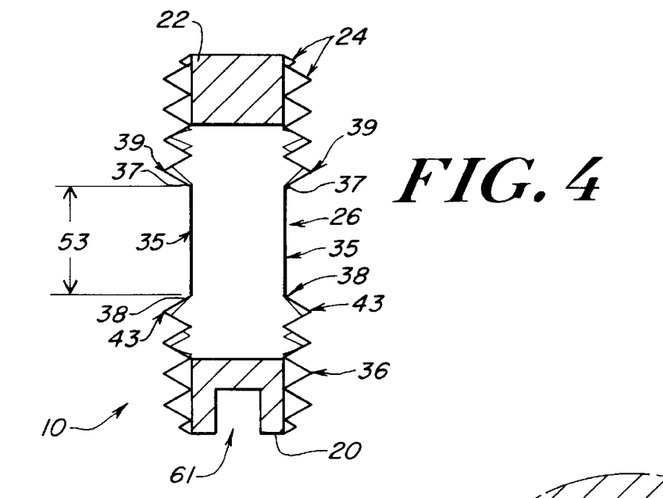
FIG. 4 is a sectional view of the implant of FIG. 2, along the lines 4—4.
Figure 5:
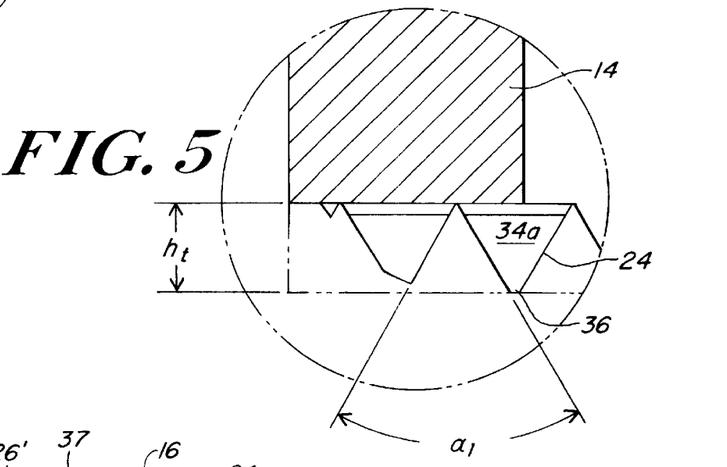
FIG. 5 is a detail view of a portion of the implant shown in FIG. 3.
Figure 6:
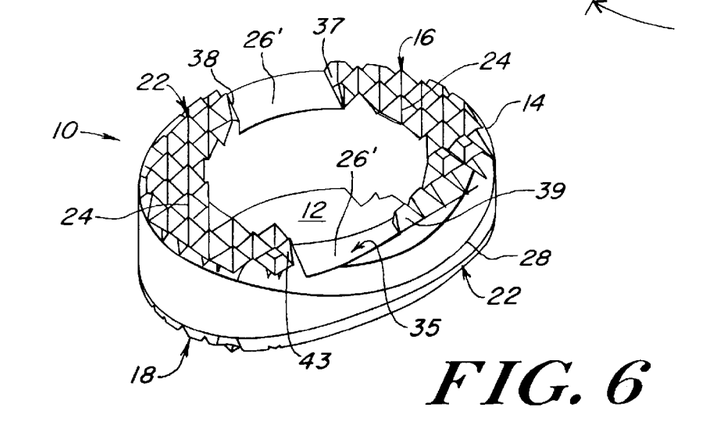
FIG. 6 is a perspective view of an alternative embodiment of an intervertebral implant constructed according to the present invention.

FIG. 4 further illustrates that the implant 10 may include a tapped or untapped hole 61 formed in anterior surface 20. The hole 61 may extend partially or completely through the body 14 into the area defined by the opening 12. The hole 61, if tapped, may be used to mate with an installation or removal tool (not shown). Alternatively, hole 61, whether tapped or untapped, can be used to fill the opening with a bone growth-promoting material.

FIGS. 6 through 11 illustrate another embodiment in which the protrusion-free zones 26' are oriented at an angle with respect to anterior-posterior axis 40. This angular orientation of zones 26', as noted above, facilitates an antero-lateral approach during a surgical installation of the device. The protrusion-free zones 26' are preferably angled with respect to the anterior-posterior axis 40 at an angle ($\alpha_2$) that is in the range of about 10 to 50 degrees, and preferably at about 30 degrees.

Figure 3:
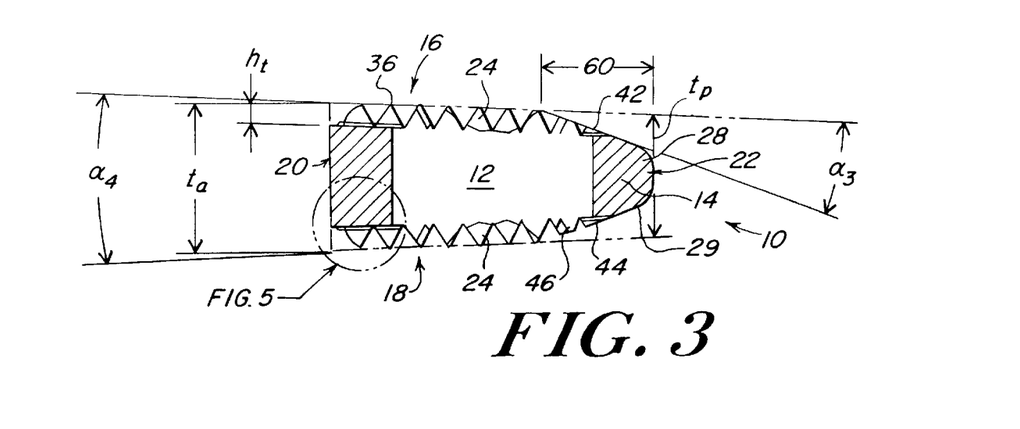
FIG. 3 is a sectional view of the implant of FIG. 2, along lines 3—3.
Figure 7:
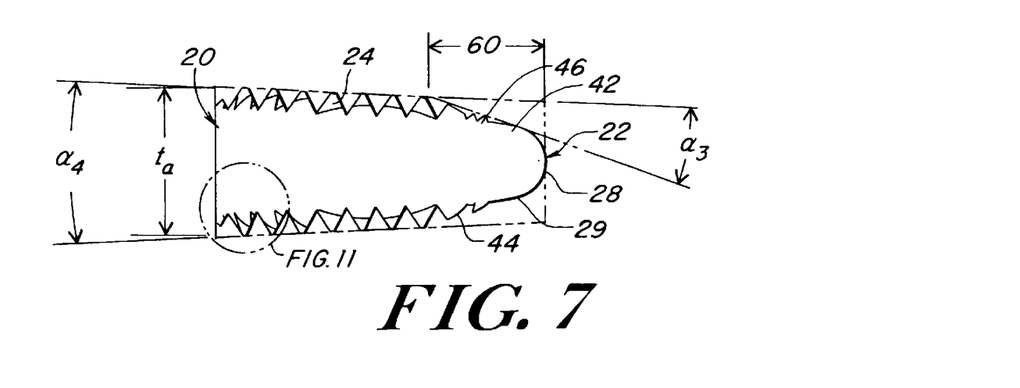
FIG. 7 is a side elevation view of the implant of FIG. 6.
Figures 8, 9:
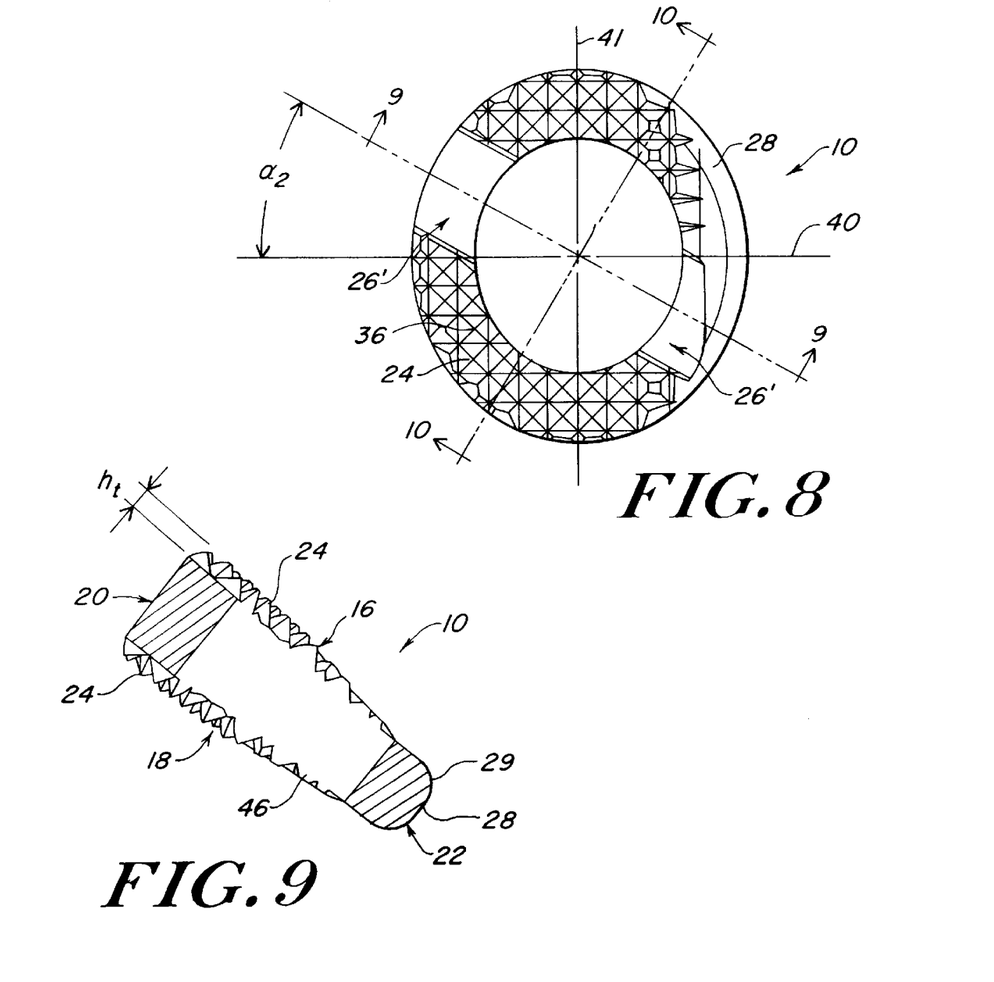
FIG. 8 is a top plan view of the implant of FIG. 6.
FIG. 9 is a sectional view of the implant of FIG. 8, along the lines 9—9.
Figure 10:
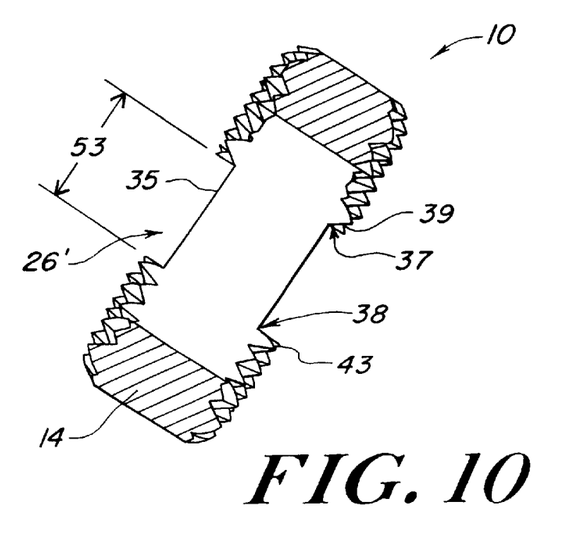
FIG. 10 is a sectional view of the implant of FIG. 8, along the lines 10—10.
Figure 11:
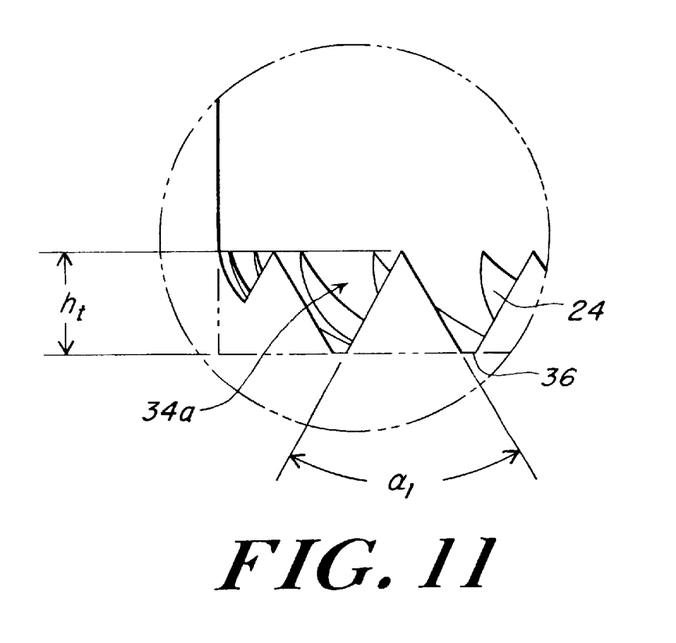
FIG. 11 is a detail view of a portion of the implant shown in FIG. 11.

The posterior end 22 of the implant 10 includes a tip 28 that has a geometry that facilitates the insertion of the implant 10 between two adjacent vertebral bodies. Preferably, this tip 28 possesses a substantially wedge-like or a bullet-like shape. The tip 28 extends over a tip region 60 that represents a distance of about 10 to 50 percent of the anterior-posterior depth of the body and it is formed by a general convergence or curvature of the opposed superior and inferior 16, 18 surfaces towards each other. As shown in FIGS. 3 and 7, the tip portion 42, 44 of superior and inferior surfaces 16, 18 is oriented at an angle ($\alpha_3$) of about 10 to 25 degrees, and most preferably at an angle of about 17.5 degrees with respect to anterior-posterior axis 40. As is further illustrated in FIGS. 3, 7, and 9, the distal most portion of the tip 28 has a generally rounded portion 29, having a radius in the range of about 2 to 10 mm.

The angled or rounded region of superior and inferior surfaces 42, 44 that form tip 28 can be created by a variety of techniques, such as by grinding. Thus, any grinding or shaping of surfaces 16, 18 that is employed to create tip 28 will necessarily result in the formation of truncated, non-pyramidal teeth 46 at locations proximal to the tip 28.

In the embodiments illustrated in FIGS. 1 through 11, the superior and inferior surfaces 16, 18 of implant 10 are generally canted such that the thickness at the anterior end ($t_a$) is greater than the thickness at the posterior end ($t_p$). This design feature enables the implant to assist in restoring the natural curvature of the spine. One of ordinary skill in the art will appreciate that the angle of the superior and inferior surfaces will vary depending upon the location in the spine at which the device is implanted. The angle ($\alpha_4$) at which surfaces 16, 18 is canted is generally in the range of about 2 to 20 degrees, and most preferably about 5 degrees.

Figure 12:
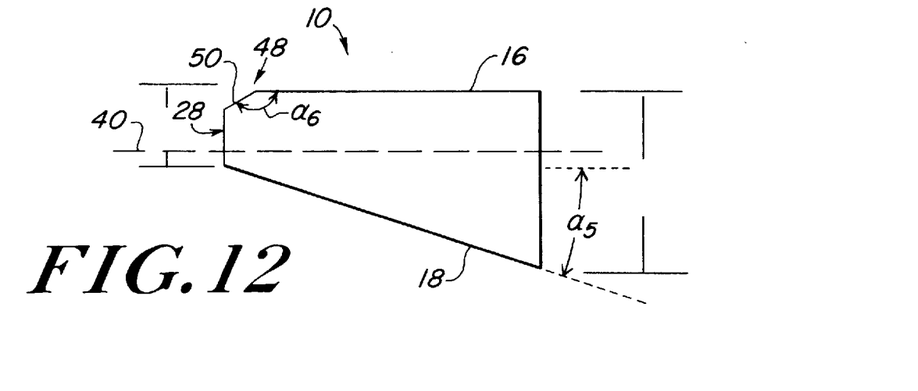
FIG. 12 is a side view illustrating a general profile of an intervertebral implant constructed according to one embodiment of the invention.

FIG. 12 illustrates an alternative embodiment that is useful in a graft for implantation between the L5 and S1 vertebrae of the spine. As illustrated, the superior surface 16 is oriented so as to be parallel to the anterior-posterior axis 40, while the inferior surface 18 is angled to conform to the end plate (not shown) of the S1 vertebral body. Accordingly, inferior surface 18 is oriented at an angle ($\alpha_5$) in the range of about 2 to 20 degrees, and most preferably about 12 degrees. FIG. 12 further illustrates that a distal portion 48 of the tip 28 is formed by a chamfered portion 50 of the superior surface 16 and the angulation of the inferior surface 18. Preferably, the chamfer of the superior surfaces formed at an obtuse angle ($\alpha_6$) of about 110 to 160 degrees with respect to the superior surface.

Figure 13:
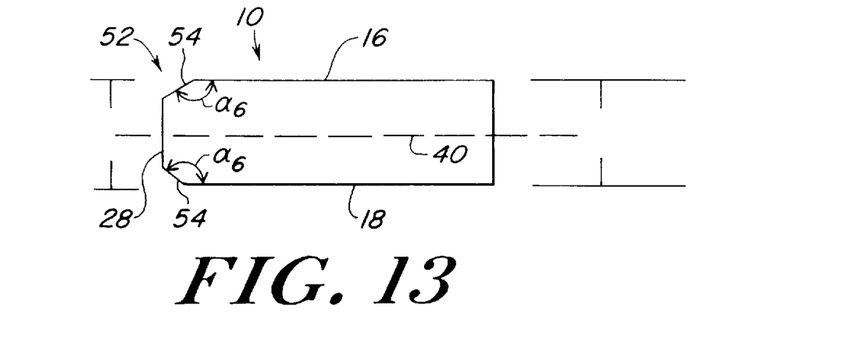
FIG. 13 is a side view illustrating a general profile of an intervertebral implant constructed according to another embodiment of the invention.

In another embodiment, illustrated in FIG. 13, both the superior and inferior surfaces 16, 18 are parallel to one another. The distal portion 52 of the tip 28 is formed by a chamfer 54 that causes the tip to form an obtuse angle ($\alpha_6$) with respect to the superior and inferior surfaces 16, 18. The obtuse angle ($\alpha_6$) is generally in the range of about 110 to 160 degrees.

Figure 14:
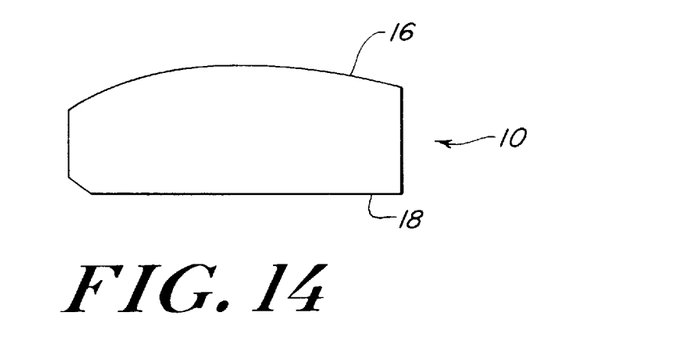
FIG. 14 is a side view illustrating a general profile of an intervertebral implant constructed according to yet another embodiment of the invention.

In yet another embodiment, illustrated in FIG. 14, the superior surface 16 has a generally dome-like profile. The surface 16 may be dome-like in both the coronal and sagittal planes, having a radius of curvature in each plane in the range of about 50 to 350 mm.

The dimensions of the implant 10 may vary, as noted above, depending upon factors such as the location in the spine at which is to be implanted, and the size of the patient. The thickness at the anterior portion of the body ($t_a$), measured from peak-to-peak of the teeth 24 is in the range of about 6 to 24 millimeters. The anterior-posterior depth 32 has dimensions in the range of about 20 to 40 millimeters while the medial width 30 has dimensions in the range of about 16 to 36 millimeters. The tooth height ($h_t$) is generally in the range of about 0.5 to 7 mm, and preferably about 1.65 mm, as measured from the superior or inferior surface 16, 18. The wall thickness 51 (FIG. 2) of body 14 is generally in the range of about 3 to 10 mm, and most preferably it is about 5 mm.

The protrusion-free zones 26, 26' generally have a depth that is interrupted by opening 12, but which extends over the entire dimension of the body in which it is oriented. The width 53 (FIG. 4) of the zones 26, 26' is generally in the range of about 1.5 to 10 mm, and most preferably about 8 mm.

The tip portion 28 extends over a distance that represents about 10 to 35 percent of the anterior-posterior depth 32 of the body 10. Thus, the tip generally has a depth of about 5 to 10 mm, and most preferably about 8 mm. Approximately 25 to 50% of the depth of the tip 28 is formed by a curved or rounded portion 29 that extends over a distance of about 2 to 10 mm.

The implant 10 of the present invention may be constructed of a variety of materials that are bio-compatible and suitable for medical applications. One preferred material from which the implant can be made is allograft bone. Those having ordinary skill in the art will readily understand that known procedures exist to harvest, sterilize, and form allograft bone into the desired sizes and shapes. Various milling and grinding techniques can be used to achieve the ultimate shape of the implant following the harvesting of bone. Other materials from which the implants can be made include metals, metal alloys, biologically compatible polymers, carbon fiber reinforced polymers, and combinations of these materials.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed:

1. An implantable bone graft, comprising:
    a solid annular body having a superior surface, an inferior surface, an anterior end, and a posterior end;
    a substantially central opening extending between the superior and inferior surfaces;
    a plurality of discrete bone-engaging teeth protruding above at least a portion of the superior and inferior surfaces, the teeth each having a base integral with one of the superior and inferior surfaces;
    a first relief on the superior surface and oriented in a desired direction to form a first tooth-free band that is not cut into the superior surface of the body;
    a second relief on the inferior surface and oriented in the desired direction to form a second tooth-free band that is not cut into the inferior surface of the body, the second tooth-free band being aligned with and formed opposite to the first tooth-free band; and
    a tip formed at the posterior end of the body by converging portions of the superior and inferior surfaces.

2. The graft of claim 1, wherein the body has a substantially ovoid shape.

3. The graft of claim 1, wherein the body has a substantially circular shape.

4. The graft of claim 1, wherein the opening is of a shape selected from the group consisting of substantially circular and substantially oval.

5. The graft of claim 4, wherein the area of the opening, adjacent the superior surface, is approximately 25 to 75 % of the area defined by the superior surface.

6. The graft of claim 1, wherein at least some of the teeth are pyramid shaped.

7. The graft of claim 6, wherein the pyramid shaped teeth have a height, measured from the superior surface of the body, in the range of about 0.5 to 7 mm.

8. The graft of claim 1, wherein the first tooth-free band is defined by the superior surface of the body and opposed first and second rows of medial superior teeth and the second tooth-free band is defined by the inferior surface of the body and opposed first and second rows of medial inferior teeth.

9. The graft of claim 8, wherein the first and second tooth-free bands each have a width in the range of about 1.5 to 10 mm.

10. The graft of claim 8, wherein each of the first and second tooth-free bands is substantially centrally disposed and aligned with an anterior-posterior axis of the body.

11. The graft of claim 8, wherein each of the first and second tooth-free bands is substantially centrally disposed and extend at an angle with respect to an anterior-posterior axis of the body.

12. The graft of claim 11, wherein the angle is in the range of about 10° to 50°.

13. The graft of claim 1, wherein a portion of each of the superior and inferior surfaces exclusive of the tip is disposed at an angle such that the thickness of the body is greater at the anterior end than at the posterior end.

14. The graft of claim 13, wherein the angle is in the range of about 2° to 20°.

15. The graft of claim 1, wherein the superior surface is oriented in a plane that extends substantially parallel to an anterior-posterior axis of the body and the inferior surface is oriented at an angle with respect to the superior surface such that the thickness of the body is greater at the anterior end than at the posterior end.

16. The graft of claim 15, wherein the angle is in the range of about 2° to 20°.

17. The graft of claim 1, wherein each of the superior and inferior surfaces is oriented in a plane that extends substantially parallel to an anterior-posterior axis of the body.

18. The graft of claim 1, wherein the tip extends over a distance representative of about 10 to 50% of the anterior-posterior depth of the body.

19. The graft of claim 18, wherein the portions of the superior and inferior surfaces that form the tip converge at an angle in the range of about 10° to 25°.

20. The graft of claim 18, wherein a distal-most end of the tip has a continuous curve with a radius in the range of about 2 to 10 mm extending over approximately 25 to 50% of the depth of the tip.

21. The graft of claim 18, wherein the tip is free of teeth.

22. The graft of claim 18, wherein a distal-most end of the tip forms an obtuse angle with the superior surface and the inferior surface.

23. The graft of claim 1, wherein the body is made from a material selected from the group consisting of allograft bone, metals, metal alloys, carbon fiber reinforced polymers, biocompatible polymers and combinations thereof.

24. An implantable spinal prosthesis, comprising:
a solid annular body having a superior surface, an inferior surface, an anterior end, and a posterior end;
a substantially central opening extending between the superior and inferior surfaces;
a plurality of discrete surface protrusions extending from at least a portion of the superior and inferior surfaces, the surface protrusions each having a base integral with one of the superior and inferior surfaces;
at least one superior protrusion-free zone on the superior surface that is not cut into the superior surface, the superior protrusion-free zone having a predetermined shape and being oriented in a desired direction;
at least one inferior protrusion-free zone on the inferior surface that is not cut into the inferior surface, the inferior protrusion-free zone having a predetermined shape and being oriented in a desired direction; and
a tip formed at the posterior end of the body by converging portions of the superior and inferior surfaces.

25. The graft of claim 24, wherein at least one superior protrusion-free zone is aligned with and formed opposite to the inferior protrusion-free zone.

26. The graft of claim 25, wherein each of the at least one superior protrusion-free zone and the at least one superior protrusion-free zone is substantially centrally disposed and is aligned with an anterior-posterior axis of the body.

27. The graft of claim 25, wherein each of the at least one superior protrusion-free zone and the at least one inferior protrusion-free zone is substantially centrally disposed and extend at an angle with respect to an anterior-posterior axis of the body.

28. The graft of claim 27, wherein each of the at least one superior protrusion-free zone and the at least one inferior protrusion-free zone extend at an angle that is substantially orthogonal to the anterior-posterior axis.

29. The graft of claim 27, wherein the angle is in the range of about 10° to 50°.

\* \* \* \* \*